United States Patent
Ko

(10) Patent No.: US 10,894,171 B2
(45) Date of Patent: Jan. 19, 2021

(54) TREATMENT DEVICE USING HIGH FREQUENCY

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 282 days.

(21) Appl. No.: 15/957,720

(22) Filed: Apr. 19, 2018

(65) Prior Publication Data

US 2018/0236256 A1 Aug. 23, 2018

Related U.S. Application Data

(62) Division of application No. 14/233,046, filed as application No. PCT/KR2012/005552 on Jul. 13, 2012, now abandoned.

(30) Foreign Application Priority Data

Jul. 15, 2011 (KR) .................. 10-2011-0070674

(51) Int. Cl.
  *A61N 5/00* (2006.01)
  *A61H 39/08* (2006.01)
  *A61N 1/06* (2006.01)
  *A61N 1/05* (2006.01)

(52) U.S. Cl.
  CPC .............. *A61N 5/00* (2013.01); *A61H 39/08* (2013.01); *A61N 1/0502* (2013.01); *A61N 1/06* (2013.01); *A61H 2201/0153* (2013.01); *A61H 2201/0184* (2013.01); *A61H 2201/10* (2013.01); *A61H 2201/1685* (2013.01); *A61H 2201/5005* (2013.01); *A61H 2201/5025* (2013.01); *A61H 2201/5035* (2013.01); *A61H 2201/5071* (2013.01); *A61H 2230/65* (2013.01)

(58) Field of Classification Search
  CPC ....................................................... A61N 5/00
  See application file for complete search history.

(56) References Cited

U.S. PATENT DOCUMENTS

| 5,383,874 A * | 1/1995 | Jackson ................. A61B 18/00 606/1 |
| 7,214,224 B2 * | 5/2007 | Goble ................ A61B 18/1206 606/34 |
| 2003/0199863 A1 * | 10/2003 | Swanson ............ A61B 18/1206 606/40 |

(Continued)

*Primary Examiner* — Kaitlyn E Smith

(57) ABSTRACT

The present invention relates to a treatment device using high frequency and provides a treatment device using high frequency comprising: a main body comprising a high frequency generation portion inside; a contact type handpiece comprising a first electrode portion for providing high frequency energy generated in the high frequency generation portion to the surface of the skin, and is detachably formed at an fastening portion of the main body; an invasive handpiece comprising a second electrode portion for providing high frequency energy generated in the high frequency generation portion to the inside of the skin, and is detachably formed at an fastening portion of the main body; and a control portion for controlling the high frequency energy provided from the high frequency generation portion to the first electrode portion or the second electrode portion.

11 Claims, 11 Drawing Sheets

(56) References Cited

U.S. PATENT DOCUMENTS

| | | | |
|---|---|---|---|
| 2008/0281254 A1* | 11/2008 | Humayun | A61B 90/98 604/22 |
| 2009/0036958 A1* | 2/2009 | Mehta | A61B 18/1477 607/99 |
| 2009/0112205 A1* | 4/2009 | McGill | A61B 18/14 606/41 |

* cited by examiner

TREATMENT DEVICE USING HIGH FREQUENCY

CROSS-REFERENCE TO RELATED APPLICATIONS

The present specification is a divisional of U.S. patent application Ser. No. 14/233,046, filed on Jan. 15, 2014, which is a U.S. National Stage of International Patent Application No. PCT/KR2012/005552, filed on Jul. 13, 2012, which claims priority to and the benefit of Korean Patent Application No. 10-2011-0070674, filed on Jul. 15, 2011, the entire contents of which are incorporated herein by reference.

TECHNICAL FIELD

The present invention relates to a treatment device using high-frequency wave, and more specifically, to a treatment device using high-frequency wave that may treat skin tissues using high-frequency energy.

RELATED ART

There are a wide range of applications of the technology of treating skins by providing energy to skins using various energy sources to deform the skin tissues or enhancing tissue characteristics. Skin treating devices using a diversity of energy sources such as laser beams, flash lamps, or ultrasonic waves have been being developed, and nowadays, research on skin treating devices adopting RF waves are intensively underway.

If high-frequency energy is supplied to a skin surface, as the electric current of the high-frequency wave changes its flowing direction, molecules in the skin are rendered to vibrate, causing friction between the molecules. Accordingly, the molecules are rotated, twisted, or collide each other, generating deep heat. Such deep heat raises the temperature of the skin tissue, reorganizing the collagen layer thereby to relieve wrinkles and enforce skin elasticity. Further, blood circulation in the skin tissue can be promoted, contributing to anti-aging or better skin condition.

Korean Patent Application Publication No. 2010-0101420 (published on Sep. 17, 2010) discloses a treating device using high-frequency waves.

Here, the high-frequency wave treatment shows different effects depending on the position of the skin to which high-frequency wave energy is provided. Accordingly, in order to achieve the optimal treatment result, the position where high-frequency waves are applied needs to be varied depending on the purposes of treatment. However, it is difficult to conduct various surgical procedures with a single piece of equipment like the conventional high-frequency treatment.

SUMMARY

Objects

The present invention has been designed to address such problems, and an object of the present invention is to provide a treatment device using high-frequency wave that may provide high-frequency energy to various positions of the skin depending on the purpose of the surgical procedure.

Solutions

The above-described objects of the present invention may be achieved by a treatment device using high-frequency wave, comprising: a main body including a high-frequency wave generating unit; a contact-type hand piece detachably provided at a coupling unit of the main body, the contact-type hand piece having a first electrode unit that provides high-frequency energy generated from the high-frequency wave generating unit to a skin surface; an invasive hand piece detachably provided at a coupling unit of the main body, the invasive hand piece having a second electrode unit that provides high-frequency energy generated from the high-frequency wave generating unit to a portion under the skin, and a controller controlling high-frequency energy provided from the high-frequency wave generating unit to the first electrode unit or the second electrode unit.

Here, the treatment device using high-frequency wave may further comprise a sensing unit sensing the type of a hand piece connected with the coupling unit, of the contact-type hand piece and the invasive hand piece.

The controller may compare a set operation mode with the type of the hand piece sensed by the sensing unit, and if determining that a hand piece corresponding to the set operation mode is not connected with the coupling unit, may generate an error signal.

If determining that the hand piece corresponding to the set operation mode is not connected with the coupling unit, the controller may perform control so that high-frequency energy is not provided from the high-frequency wave generating unit to the hand piece.

Or, the controller may control the high-frequency wave generating unit in different modes from each other depending on the type of the hand piece sensed by the sensing unit.

Meanwhile, the contact-type hand piece may include a first sensor that senses a contact state between the first electrode unit and the skin, and if determining that the contact state between the first electrode unit and the skin is poor, based on information sensed by the first sensor, the controller may generate a contact-poor signal.

Meanwhile, the invasive hand piece may further include a driving unit that provides a driving force for allowing the second electrode unit to be inserted into the skin, and if determining that the set operation mode is not an operation mode corresponding to the invasive hand piece, the controller may perform control so that no driving force is provided from the driving unit to the second electrode unit.

Or, the second electrode unit may be exchangeably provided at the invasive hand piece, and the invasive hand piece may further include a second sensor that senses the type of the second electrode unit.

The controller may compare the set operation mode with the type of the second electrode unit sensed by the second sensor, and if determining that the second electrode unit provided at the invasive hand piece does not correspond to the set operation mode, may generate an error signal. Or, the controller may control the high-frequency wave generating unit in different modes from each other depending on the type of the second electrode unit sensed by the second sensor.

On the other hand, the above-described objects of the present invention may be achieved by a treatment device using high-frequency wave, comprising: a high-frequency wave generating unit provided in a main body; a contact-type hand piece connected to the main body, the contact-type hand piece having a first electrode unit that provides high-frequency energy generated from the high-frequency wave generating unit to a skin surface; an invasive hand piece connected to the main body, the invasive hand piece having a second electrode unit that provides high-frequency energy generated from the high-frequency wave generating unit to a portion under the skin; and a controller performing control so that high-frequency energy generated from the high-frequency wave generating unit is selectively provided to the first electrode unit or the second electrode unit.

Here, the treatment device using high-frequency wave may further comprise a sensing unit sensing the type of a hand piece used by a user, of the contact-type hand piece and the invasive hand piece.

The controller may compare a set operation mode with the type of the hand piece sensed by the sensing unit, and if determining that a hand piece not corresponding to the set operation mode is being used, may generate an error signal.

Further, if determining that a hand piece not corresponding to the set operation mode, the controller may perform control so that high-frequency energy is not provided from the high-frequency wave generating unit to the hand piece.

The controller may control the high-frequency wave generating unit in different modes from each other depending on the type of the hand piece sensed by the sensing unit.

Advantageous Effects

According to the present invention, high-frequency energy may be applied to a proper position of the skin depending on the purpose of a surgical procedure. Accordingly, the effect of the surgical procedure may be enhanced. Further, various surgical procedures may be carried out with a single device, thus saving a user costs for purchasing treating devices.

DETAILED DESCRIPTION OF EMBODIMENTS

Hereinafter, a treatment device using high-frequency wave according to an embodiment of the present invention is described in detail with reference to the accompanying drawings. The relationship in position between components is described based on the drawings. For ease of description, the drawings may be simplified or exaggerated as necessary. Accordingly, the present invention is not limited to the embodiment, and other various devices may be added or changes or omissions may also be made thereto.

Figure 1:
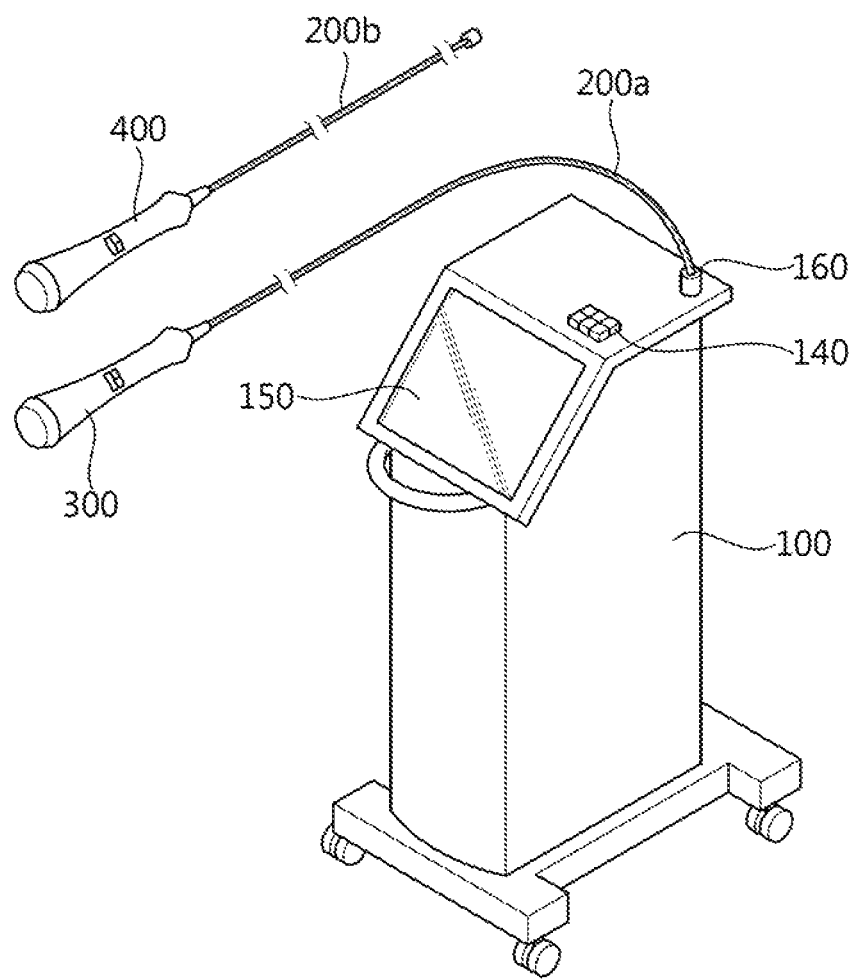
FIG. 1 is a perspective view illustrating a treatment device using high-frequency wave according to a first embodiment of the present invention.

FIG. 1 is a perspective view illustrating a treatment device using high-frequency wave according to a first embodiment of the present invention. A treatment device using high-frequency wave according to an embodiment of the present invention, as shown in FIG. 1, includes a main body 100, a contact-type hand piece 300 and an invasive hand piece 400 that are detachably provided at the main body 100.

The main body 100 includes a power supply (not shown) to receive power from outside. On an outside surface of the main body 100 are provided a control panel 140 for operating the driving of the treatment device using high-frequency wave and a display 150 for displaying the driving to a user. In the main body 100 is provided a high-frequency wave generating unit 110 for generating high-frequency energy using power supplied from the power supply. On an outside surface of the main body 100 is formed a coupling unit for coupling the contact-type hand piece 300 with the invasive hand piece 400.

The contact-type hand piece 300 and the invasive hand piece 400 respectively include bodies 310 and 410 and electrode units 320 and 420. The bodies 310 and 410 form the frames of the hand pieces 300 and 400 and are configured for a user to be able to grasp. On outside surfaces of the bodies 310 and 410 may be formed manipulating units 330 and 430 that allow a user to simply manipulate the driving of the hand pieces while a surgical procedure is in process.

The contact-type hand piece 300 and the invasive hand piece 400 may have their respective electrode units 320 and 420 at their respective ends. The electrode units 320 and 420 may provide high-frequency energy coming from the high-frequency wave generating unit 110 to the skin. The first electrode unit 320 provided in the contact-type hand piece 300 and the second electrode unit 420 provided in the invasive hand piece 400 may differ in shape from each other, and detailed description thereof will be given below.

The contact-type hand piece 300 and the invasive hand piece 400 are connected to the main body 100 via cables 200a and 200b, respectively. The cables 200a and 200b, respectively, include high-frequency wave delivering units 210a and 210b and signal lines 220a and 220b. The high-frequency wave delivering unit electrically connects the high-frequency wave generating unit 110 of the main body 100 with the electrode unit 320 or 420 of the hand piece 300 or 400, thereby forming a high-frequency wave circuit that may provide high-frequency energy to the skin. The signal line transmits/receives various control signals or sensed signals between the main body 100 and the hand piece 300 or 400. For example, the signal line may transmit a control signal for a user to perform manipulation through the hand piece's manipulating unit and a signal sensed by a sensor provided in the hand piece to the controller in the main body. Or, the signal line may transfer a control signal for the controller of the main body to control the operation of the hand piece to the hand piece.

As illustrated in FIG. 1, in this embodiment, the contact-type hand piece 300 and the invasive hand piece 400 have their respective cables 200a and 200b extended from their respective ends. A coupling structure is provided at an end of each cable 200a or 200b so as to connect with the coupling unit 160 of the main body 100. Accordingly, a user may conduct a surgical procedure, with the coupling unit 160 connected with the coupling structure of his desired one of the contact-type hand piece 300 and the invasive hand piece 400. Further, for a different surgical procedure, the user may replace the coupled hand piece with the other hand piece while disconnecting the coupled hand piece from the coupling unit 160.

In the above-embodiment, each hand piece has a separate cable and the coupling unit is provided on the outside surface of the main body. However, the cable may be connected to the main body and the cable unit may be provided at the end of the cable, so that each hand piece is connected to the cable of the main body.

Figure 2:
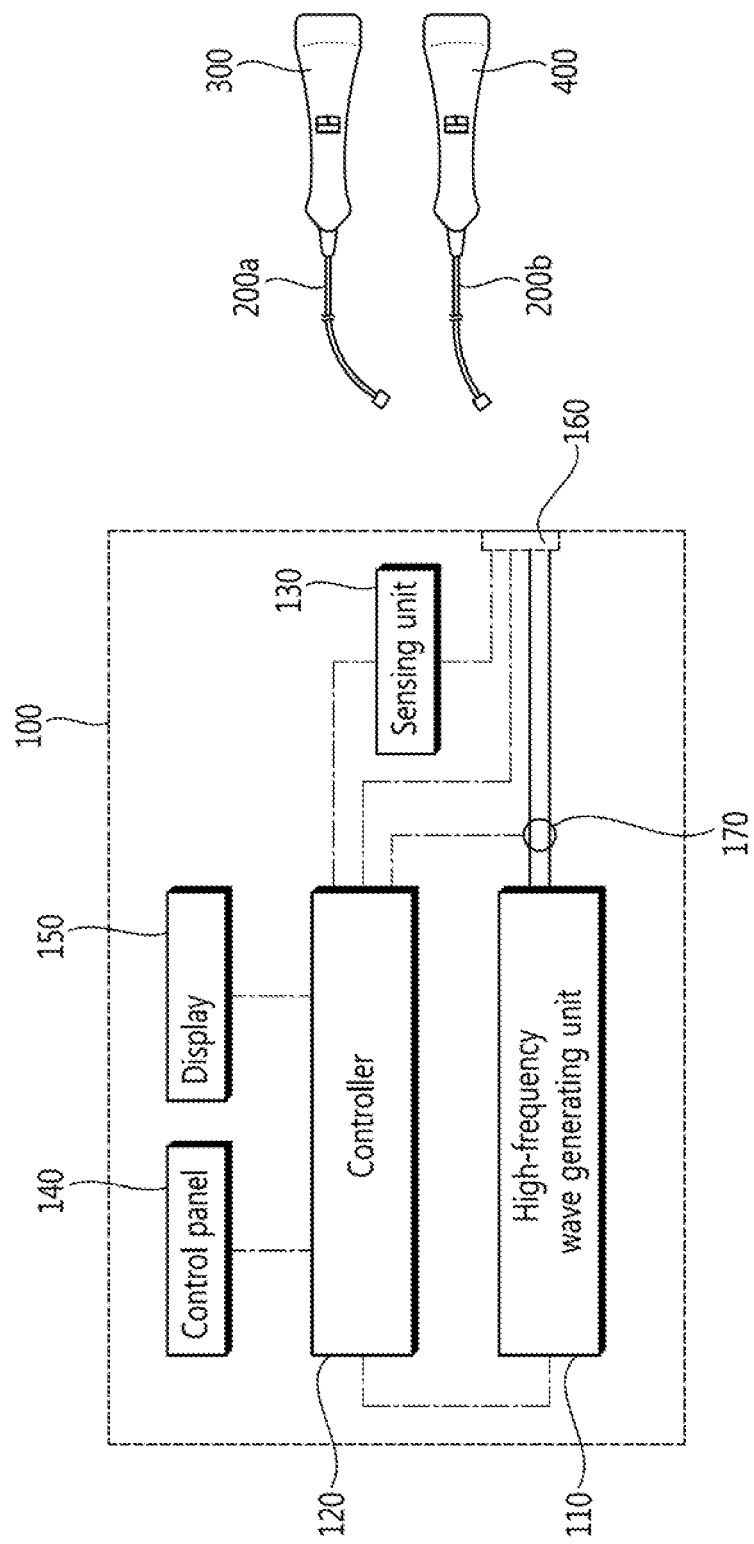
FIG. 2 is a block diagram schematically illustrating the internal structure of the main body of FIG. 1.

FIG. 2 is a block diagram schematically illustrating the internal structure of the main body of FIG. 1. Hereinafter, the structure of the main body according to an embodiment of the present invention is described in further detail with reference to FIG. 2.

As described earlier, the main body 100 includes various elements including a control panel 140 for a user to set an operation mode of the treatment device using high-frequency wave, a display 150 for displaying various pieces of information including the operations of the treating device to the user, and a high-frequency wave generating unit 110 for generating high-frequency energy. The main body also includes a controller 120 for controlling the elements.

For example, if the user sets an operation mode through the control panel 140, information on the mode is transmitted to the controller 120. The controller 120 controls the high-frequency wave generating unit 110 and other elements so that an operation corresponding to the set operation mode is performed according to the mode. Further, the controller 120 may display, to the user through the display 150, the operations performed by the treatment device using high-frequency wave and information sensed from various sensors.

Further, the main body 100 may include a sensing unit 130 for sensing the type of a hand piece connected to the coupling unit 160. The sensing unit 130 is connected to the coupling unit 160 via, e.g., a signal line and identifies whether the hand piece currently connected with the main body 100 is the contact-type hand piece 300 or the invasive hand piece 400. Information on the connected hand piece, sensed by the sensing unit 130, is transmitted to the controller 120.

In general, the contact-type hand piece 300 that provides high-frequency energy to a surface of the skin and the invasive hand piece 400 that provides high-frequency energy to a portion under the skin have different configurations from each other and are configured to control all of wave generating modules 111, 112, and 113. In case the invasive hand piece 400 is sensed to be installed, the controller 120 may control only some of multiple high-frequency wave generating modules to be driven. Or, in case the contact-type hand piece 300 is sensed to be installed, the controller 120 may control the high-frequency wave generating unit 110 to generate a first frequency of high-frequency energy, and in case the invasive hand piece 400 is sensed to be installed, the controller 120 may control a second frequency of high-frequency energy to be generated. Or, the controller 120 may control a circuit device such as a relay device 170 positioned on a path along which high-frequency energy is delivered to conduct various different control operations, such as, e.g., selectively blocking each path through which high-frequency energy is transferred or switching a path to another path.

Meanwhile, in case a hand piece not corresponding to a set operation mode is connected (for example, when a mode for using the invasive hand piece is set while the contact-type hand piece is coupled), a desired surgical procedure may be difficult to carry out, and the main body or hand piece may be damaged as well.

Accordingly, the controller 120 compares a set operation mode with the type of the hand piece sensed by the sensing unit 130, and if the coupled hand piece is not the one corresponding to the set operation mode, generates an error signal to alert the user. At this time, the error signal may be displayed on the screen through the display 150, or may be delivered to the user as an alert sound.

Further, if the controller 120 determines that a hand piece not corresponding to a set operation mode is connected, the controller 120 may control high-frequency energy not to be provided from the high-frequency wave generating unit 110. Specifically, the controller 120 may forcedly stop the operation of the high-frequency wave generating unit 110 or cut off the path along which the high-frequency energy is delivered from the high-frequency wave generating unit 110.

As such, the controller 120 may not only control various elements so that an appropriate surgical procedure may be performed based on information on a hand piece sensed by the sensing unit but may effectively prevent a malfunction that may occur when two different types of hand pieces are used, as well.

Hereinafter, the operation of a treating device with a contact-type hand piece according to an embodiment of the present invention is described in greater detail with reference to FIGS. 3 and 5.

Figure 3:
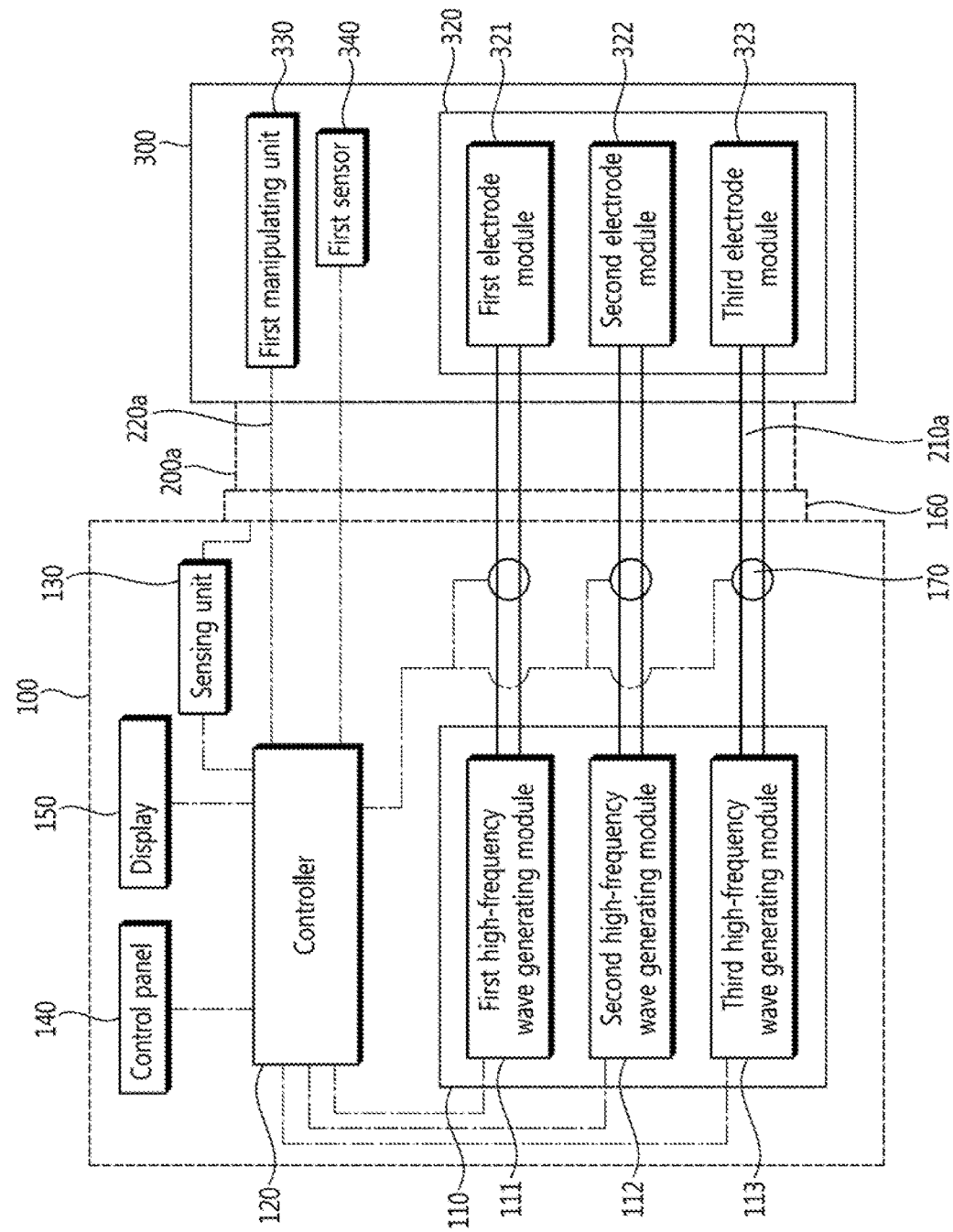
FIG. 3 is a block diagram schematically illustrating an example where a contact-type hand piece is connected with a main body as shown in FIG. 1.
Figure 4:
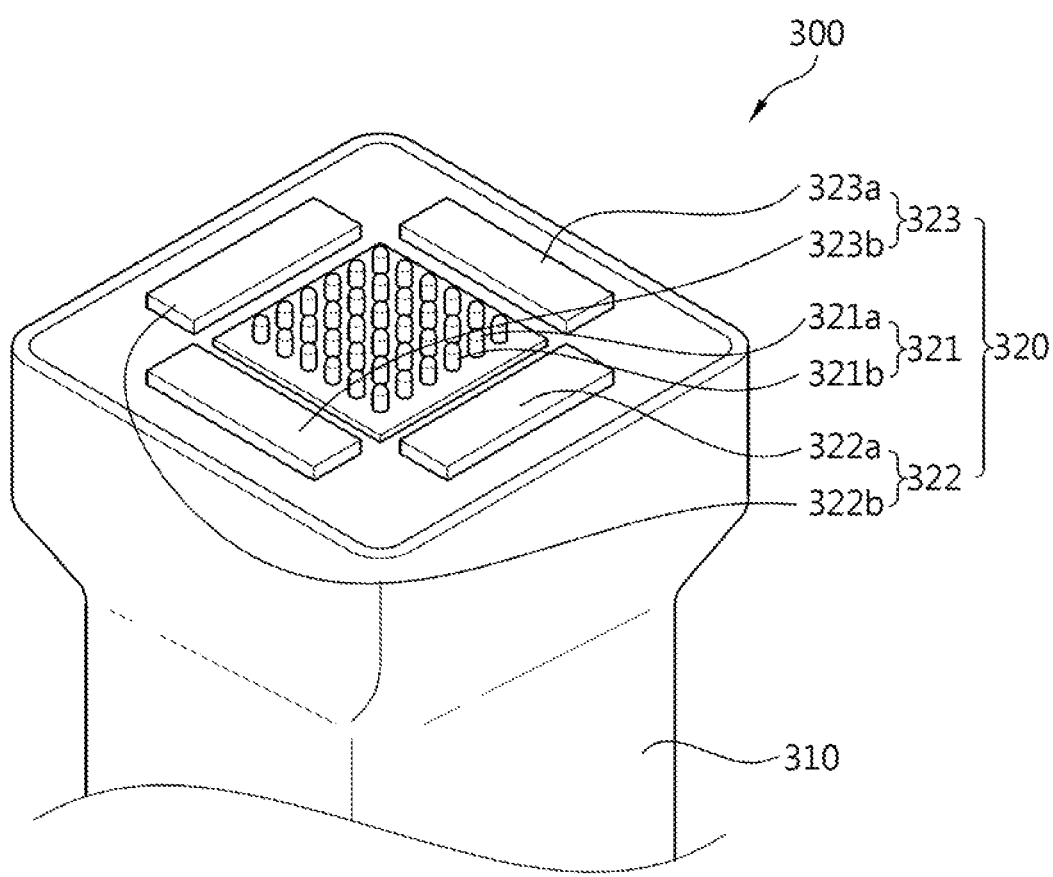
FIG. 4 is a perspective view illustrating the shape of an end of the contact-type hand piece of FIG. 3.
Figure 5:
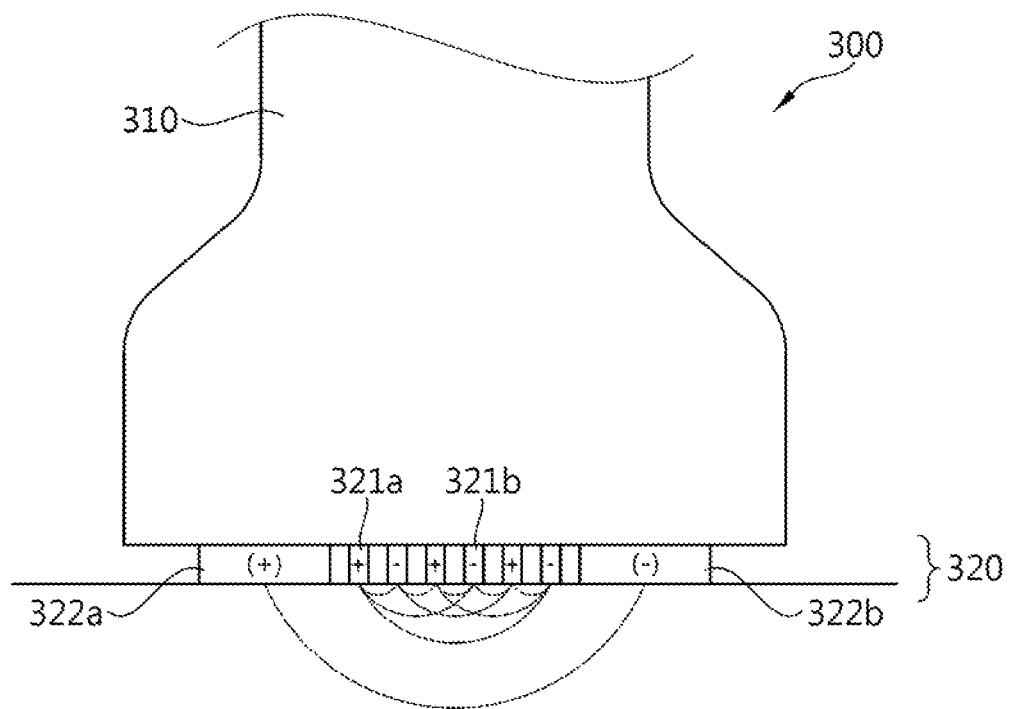
FIG. 5 is a cross-sectional view illustrating an example where skin is treated using the contact-type hand piece of FIG. 4.

FIG. 3 is a block diagram schematically illustrating an example where a contact-type hand piece is connected with a main body as shown in FIG. 1, FIG. 4 is a perspective view illustrating the shape of an end of the contact-type hand piece of FIG. 3, and FIG. 5 is a cross-sectional view illustrating an example where skin is treated using the contact-type hand piece of FIG. 4.

As illustrated in FIG. 3, the contact-type hand piece 300 has a first manipulating unit 330 that helps a user easily manipulate the operation of the contact-type hand piece 300 during a surgical procedure. An end of the contact-type hand piece 300 has a first electrode unit 320 that provides high-frequency energy to a skin surface.

The first electrode unit 320 includes multiple electrode modules. Each electrode module includes at least one or more positive electrode and negative electrode. As illustrated in FIGS. 3 to 5, the first electrode unit 320 includes a first electrode module 321 and a second electrode module 322 and a third electrode module 323 that are positioned at an external side of the first electrode module 321. At this time, each electrode module may have an end shaped as a plane or a round that enables contact with the skin by a predetermined area.

The first electrode module 321, as illustrated in FIG. 4, includes a plate-shaped supporting plate, multiple positive electrodes 321a and multiple negative electrodes 321b that are arranged on the supporting plate. The second electrode module 322 and the third electrode module 323 are positioned at both sides so that their respective positive electrodes 322a and 323a are opposite their respective negative electrodes 322b and 323b with respect to the first electrode module 321. At this time, the direction of arrangement of the positive and negative electrodes 322a and 322b of the second electrode module 322 may be perpendicular to the direction of arrangement of the positive and negative electrodes 322a and 322b of the third electrode module 323.

Meanwhile, the high-frequency wave generating unit 110 of the main body 100 may include a first high-frequency wave generating module 111, a second high-frequency wave generating module 112, and a third high-frequency wave generating module 113. Accordingly, the first to third high-frequency wave generating modules are electrically connected with the first to third electrode modules, respectively, to form their respective independent paths and provide high-frequency energy to their respective electrode modules.

At this time, the high-frequency wave generating modules are configured to generate different frequencies of high-frequency energy from each other. Accordingly, if high-frequency energy is supplied from the high-frequency wave generating unit 110 with the first electrode unit 320 brought in contact with the skin surface, the high-frequency energy provided from the first high-frequency wave generating module 111 configures an independent circuit through the positive and negative electrodes of the first electrode module 321, the high-frequency energy provided from the second high-frequency wave generating module 112 configures an independent circuit with the positive and negative electrodes of the second electrode module 322, and the high-frequency energy provided from the third high-frequency wave generating module 113 configures an independent circuit with the positive and negative electrodes of the third electrode module 323 (refer to FIG. 5). Accordingly, the position of the skin where treatment is performed may be iteratively applied high-frequency energy from multiple electrode modules.

The invasion depth of the high-frequency energy provided to the skin through each electrode module is determined depending on the distance between the positive and negative electrodes of the electrode module. Accordingly, the invasion depth of high-frequency energy provided from each electrode module may be diversified by making the distance between the positive and negative electrodes of the second electrode module different from the distance between the positive and negative electrodes of the third electrode module (refer to FIG. 5).

Meanwhile, the controller 120, if an operation mode is set from the control panel 140 as described above, compares the set operation mode with hand piece information sensed by the sensing unit 130. In the case illustrated in FIG. 3, if the operation mode is determined to use the invasive hand piece 400, the controller 120 may inform the occurrence of an error to a user through the display 150 or a separate alert sound. The controller 120 may restrict the operation of the high-frequency wave generating unit or may block the path where high-frequency energy is delivered from the high-frequency wave generating unit 110. However, in case the operation mode is determined to use the contact-type hand piece 300, the controller 120 controls various elements including the high-frequency wave generating unit 110 to be operated.

Here, the controller 120 may be configured to individually control each of the multiple high-frequency wave generating modules 111, 112, and 113 of the high-frequency wave generating unit 110. In such case, the controller 120 controls the output of high-frequency energy that is generated from each high-frequency wave generating module and may control the amount of high-frequency energy provided, depending on the skin invasion depth. Accordingly, more various procedures may be fulfilled under the control of the controller 120.

Further, the contact-type hand piece 300 may include a first sensor 340 that senses the state of contact between the first electrode unit 320 and the skin. At this time, the first sensor 340 may be configured as a pressure sensor or impedance sensor that is provided at an end of the contact-type hand piece 300.

The contact state information sensed by the first sensor 340 may be transferred to the controller 120. The controller 120, if determining that the skin contact state of the first electrode unit 320 to the skin is poor from the first sensor 340, generates a contact poor signal to conduct control so that it can be delivered to a user through the display 150 or a separate alert sound.

As described above, the contact-type hand piece according to this electrode module includes three electrode modules that respectively provide different frequencies of high-frequency energy, but this is merely an example. The present invention is not limited to a specific number of electrode modules. For example, the contact-type hand piece may be configured to provide one piece of high-frequency energy.

Hereinafter, the operation of a treating device with an invasive hand piece according to an embodiment of the present invention is described in further detail with reference to FIGS. 6 and 7.

Figure 6:
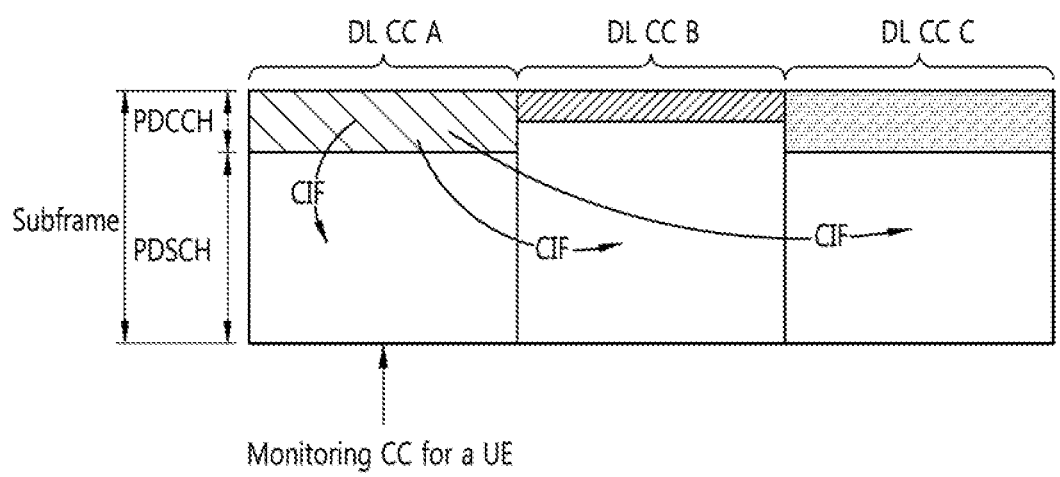
FIG. 6 is a block diagram schematically illustrating an example where the invasive hand piece is coupled with the main body of FIG. 1.
Figure 7:
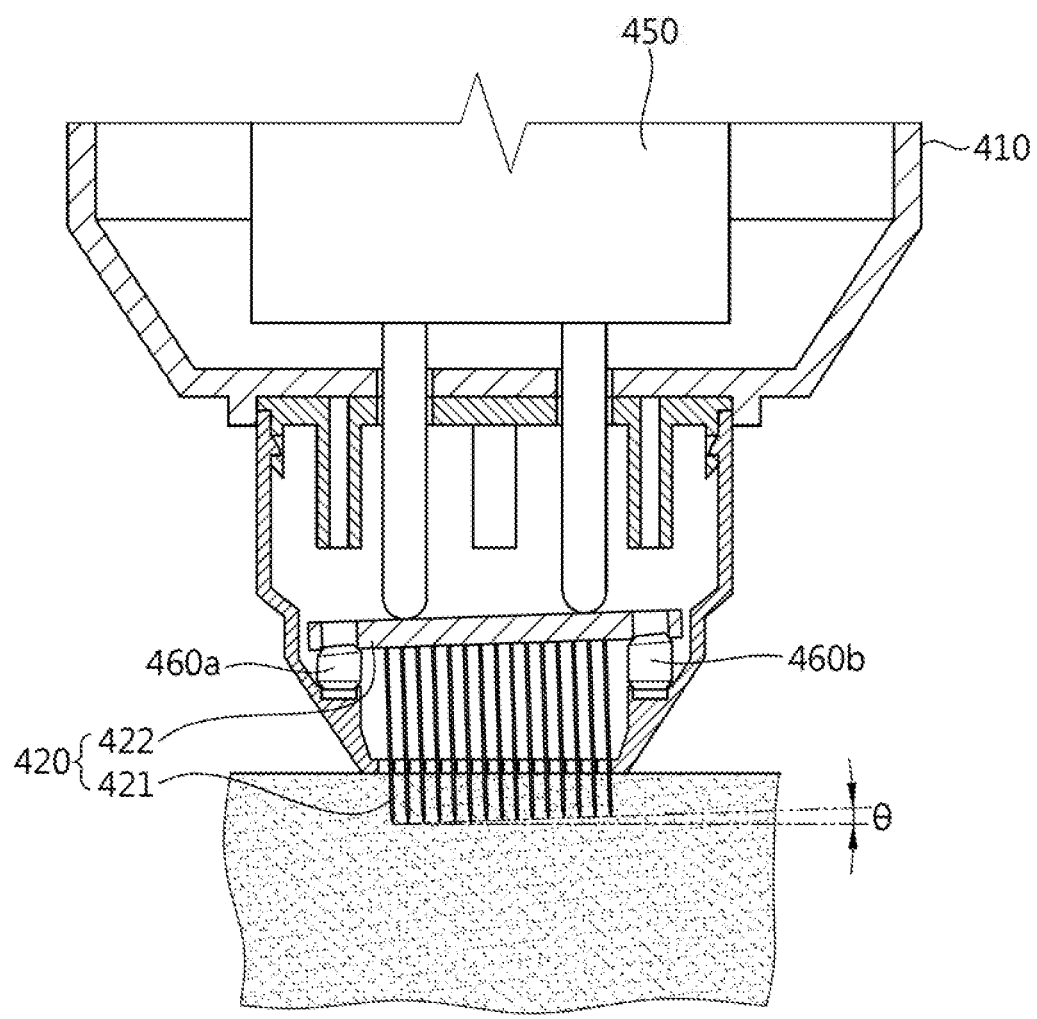
FIG. 7 is a cross-sectional view illustrating the internal structure of the invasive hand piece of FIG. 6.

FIG. 6 is a block diagram schematically illustrating an example where the invasive hand piece is coupled with the main body of FIG. 1, and FIG. 7 is a cross-sectional view illustrating the internal structure of the invasive hand piece of FIG. 6.

As illustrated in FIG. 6, the invasive hand piece 400 includes a second manipulating unit 430 that enables a user to easily manipulate the operation of the hand piece during a surgical procedure. An end of the invasive hand piece 400 includes a second electrode unit 420 to provide high-frequency energy to a portion under the skin such as subcutaneous tissue.

The second electrode unit 420 includes multiple needles 421 with sharp ends at the plate 422. The needles are inserted through the skin into an internal side during a surgical procedure. In this electrode module, the end of the needle may be configured to have a thickness of 100 um or less so as to minimize a patient's pain while enabling the needle to easily penetrate into the skin. The outside surface of the needle 421 may be formed of an insulating material except for its end so that high-frequency energy may be provided to the skin through the end.

As such, the second electrode unit 420, as illustrated in FIG. 7, is provided to be movable by receiving a driving force from the driving unit 450. Accordingly, if the driving unit 450 is driven by manipulating the second manipulating unit 430 with the second electrode unit 420 brought in contact with the skin, the multiple needles are moved and inserted into a portion under the skin.

At this time, in case the multiple needs 21 are inserted into the skin at the same time, the needles 21 may be difficult to penetrate into the skin and the patient may have more pain. Accordingly, in the instant embodiment, a separate tilting unit is provided to enable the multiple needles to sequentially penetrate into the skin, inclined at a predetermined angle θ.

In this embodiment, the tilting unit includes elastomers 460a and 460b arranged at a rear surface of the plate where the multiple needles are disposed. At this time, the elastomers 460a and 460b are configured so that the elastic modulus at, at least, one position of the rear surface of the plate 422 of the second electrode unit 420 is different from the elastic modulus at an adjacent position. Accordingly, if the driving unit 450 is driven with the second electrode unit 420 brought in contact with the skin, the needle that is located at the position where the elastic modulus of the elastomers 460*a* and 460*b* is large first penetrates into the skin surface, and the other needles sequentially start penetration.

As illustrated in FIG. 6, the tilting unit according to this electrode module uses multiple elastomers 460 and may be configured so that each elastomer 460 has a different elastic modulus from the others. However, this is merely an example, and the tilting unit may be configured to have a single elastomer that has different elastic moduli from each other at different positions. Or, other various configurations of elastomers may be used to leave the multiple needles to penetrate into the skin surface, inclined.

Meanwhile, the second electrode unit 420 having a plate where multiple needles are formed may be detachably provided at an end of the invasive hand piece 400. Accordingly, among the multiple modules having different numbers or patterns of arrangement of the needles depending on the position or purpose of a surgical procedure, an appropriate one may be selected to configure the second electrode unit 420, thereby enabling various surgical procedures.

At this time, the invasive hand piece 400 may have a second sensor 440 that may sense the type of the second electrode unit 420. Whenever the second electrode unit 420 is exchanged or surgical procedures are conducted, information on the second electrode unit 420, sensed by the second sensor 440, may be transmitted to the controller.

Meanwhile, the controller 120, if an operation mode is set by the control panel 140 as described above, compares hand piece information sensed by the sensing unit 130 with the operation mode. In the example illustrated in FIG. 6, if the operation mode is determined to use the contact-type hand piece 300, the controller 120 may deliver the occurrence of an error to a user through the display 150 or a separate alert sound. The controller 120 may limit the operation of the high-frequency wave generating unit 110 or block the path along which high-frequency energy is delivered from the high-frequency wave generating unit 110. Or, the controller 120 may control a driving force not to be provided from the driving unit 450 to the second electrode unit 420 by limiting the driving of the driving unit 450 of the invasive hand piece 400 or cutting off the path where a driving force is transferred from the driving unit 450 to the second electrode unit.

However, if the operation mode is determined to use the invasive hand piece 400, the controller 120 controls various elements including the high-frequency wave generating unit 110 to operate.

As illustrated in FIG. 6, in the instant embodiment, if, among the multiple high-frequency wave generating modules of the high-frequency wave generating unit 110, the invasive hand piece 400 is used, only a single high-frequency wave generating module is configured to be put in use. Accordingly, the controller 120 may perform control so that a single high-frequency wave generating module alone is driven to generate high-frequency energy while the remaining high-frequency wave generating modules are limited in use or the path along which high-frequency energy is delivered therefrom is cut off.

However, although the circuit illustrated in FIG. 6, where the high-frequency wave generating unit 110 and the invasive hand piece 400 are connected is configured so that the second electrode unit is electrically connected with one high-frequency wave generating module, this is merely an example provided for convenience of description, and the instant invention can be designed in other various manners.

Further, the controller 120 may control the high-frequency wave generating unit 110 in different modes based on the information on the second electrode unit sensed by the second sensor. For example, the controller 120, in case the second electrode unit 420 is coupled having needles spaced apart at a wide distance, may control the high-frequency wave generating unit 110 to generate a high output of energy. The controller 120, in case the second electrode unit 420 is coupled whose needles are arranged at a narrow distance, may control the high-frequency wave generating unit 110 to generate a low output of energy.

Or, the controller 120 compares the set operation mode with the information on the second electrode unit 420, and if the structure of the second electrode unit 420 currently provided is determined not to correspond to the set operation mode, the controller 120 performs control so that an error signal is generated to instruct a user to replace the second electrode unit 420.

As described above, the treating device according to this embodiment is configured to interchangeably use the contact-type hand piece 300 and the invasive hand piece 400. Here, the controller controls various elements of the main body based on the type of a hand piece to be coupled, thereby enabling an optimized surgical procedure. Further, the controller may prevent any security issue that may happen when different hand pieces are selectively used.

Hereinafter, a method of controlling a treatment device using high-frequency wave according to a first embodiment, as described above in connection with FIGS. 8 and 9 is described.

Figure 8:
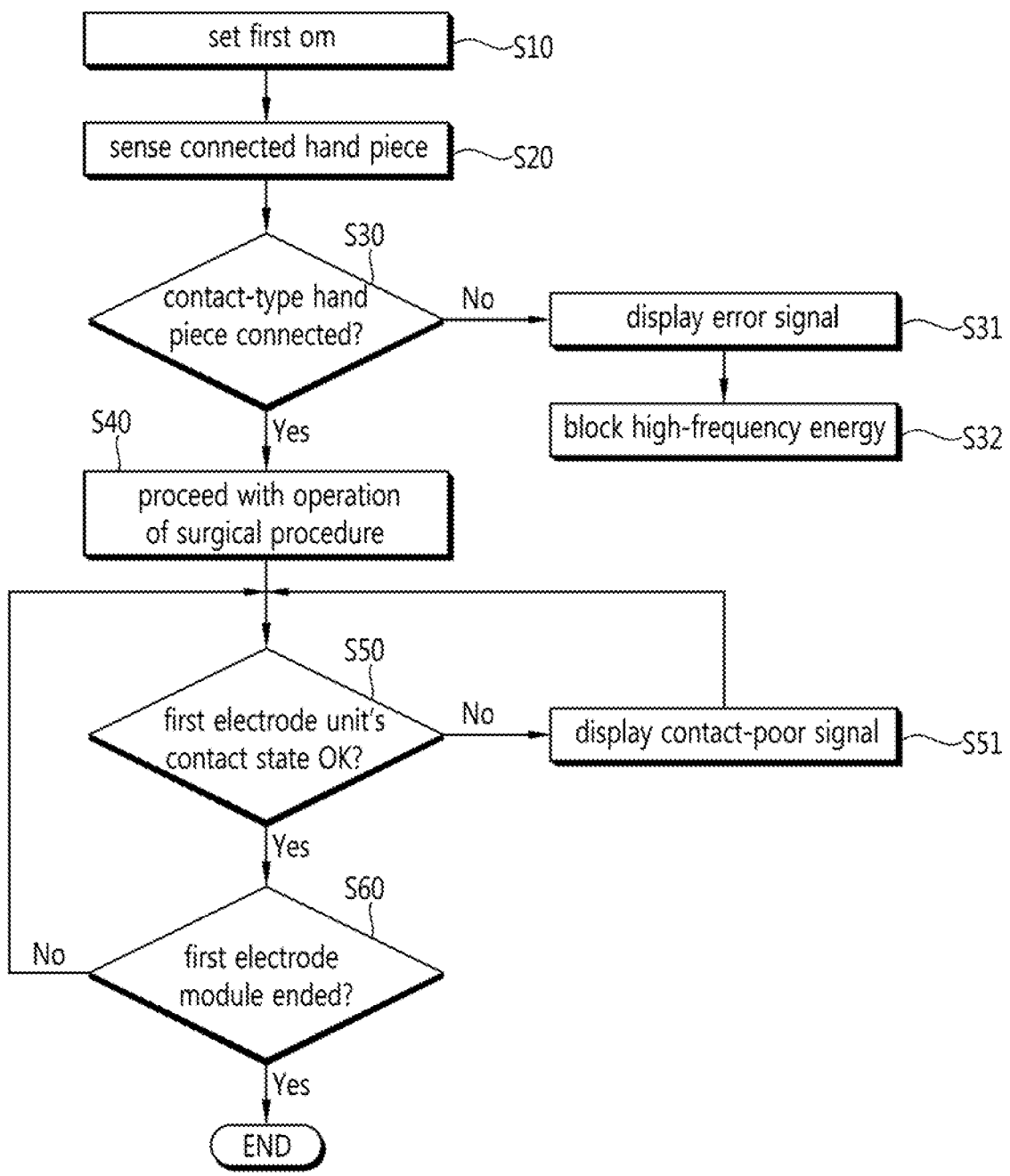
FIG. 8 illustrates a controlling method performed by a treatment device using high-frequency wave according to a first operation mode, in accordance with a first embodiment of the present invention.

FIG. 8 illustrates a controlling method performed by a treatment device using high-frequency wave according to a first operation mode, in accordance with a first embodiment of the present invention. As illustrated in FIG. 8, a user sets the device to operate in a first operation mode through the control panel 140 so as to proceed with a surgical procedure (S10). At this time, the first operation mode, for ease of description, is assumed to be an operation mode that is in process using a contact-type hand piece.

If the operation mode is set, it is sensed whether the hand piece coupled with the coupling unit 160 is the contact-type hand piece 300 or the invasive hand piece 400 (S20). Step S20 is performed by the sensing unit 130, and information on the type of the hand piece sensed is provided to the controller 120 (S30).

The controller 120, if the sensed hand piece is determined to be the invasive hand piece 400, generates an error signal and notifies the user through the display 150 or a separate alert signal (S31). Further, the controller 120 may put a limit to high-frequency energy being provided to the coupled invasive hand piece so that the invasive hand piece 400 initiates its operation (S32). This may be achieved in various manners, such as, by limiting the operation of the high-frequency wave generating unit 110, blocking the path along which high-frequency energy is delivered, or restricting the operation of the driving unit 450 of the invasive hand piece 400.

On the other hand, if the sensed hand piece is determined to be the contact-type hand piece 300, the controller controls various elements so that an operation for a surgical procedure may be normally conducted (S40).

Meanwhile, while the surgical procedure is in process, the first sensor 340 provided in the contact-type hand piece 300 grasps whether the surgical procedure runs normally by sensing the contact state between the first electrode unit 320 and the skin (S50). At this time, if the contact state between the first electrode unit 320 and the skin is determined by the first sensor 340 to be not good, the controller 120 generates a contact-poor signal to let a user know (S51). Such operation of the first sensor 340 may be periodically or continuously performed while the surgical procedure is on the go.

Thereafter, determining whether the set first operation mode reaches the operation end time, the controller may terminate the operation of various elements (S60).

Figure 9:
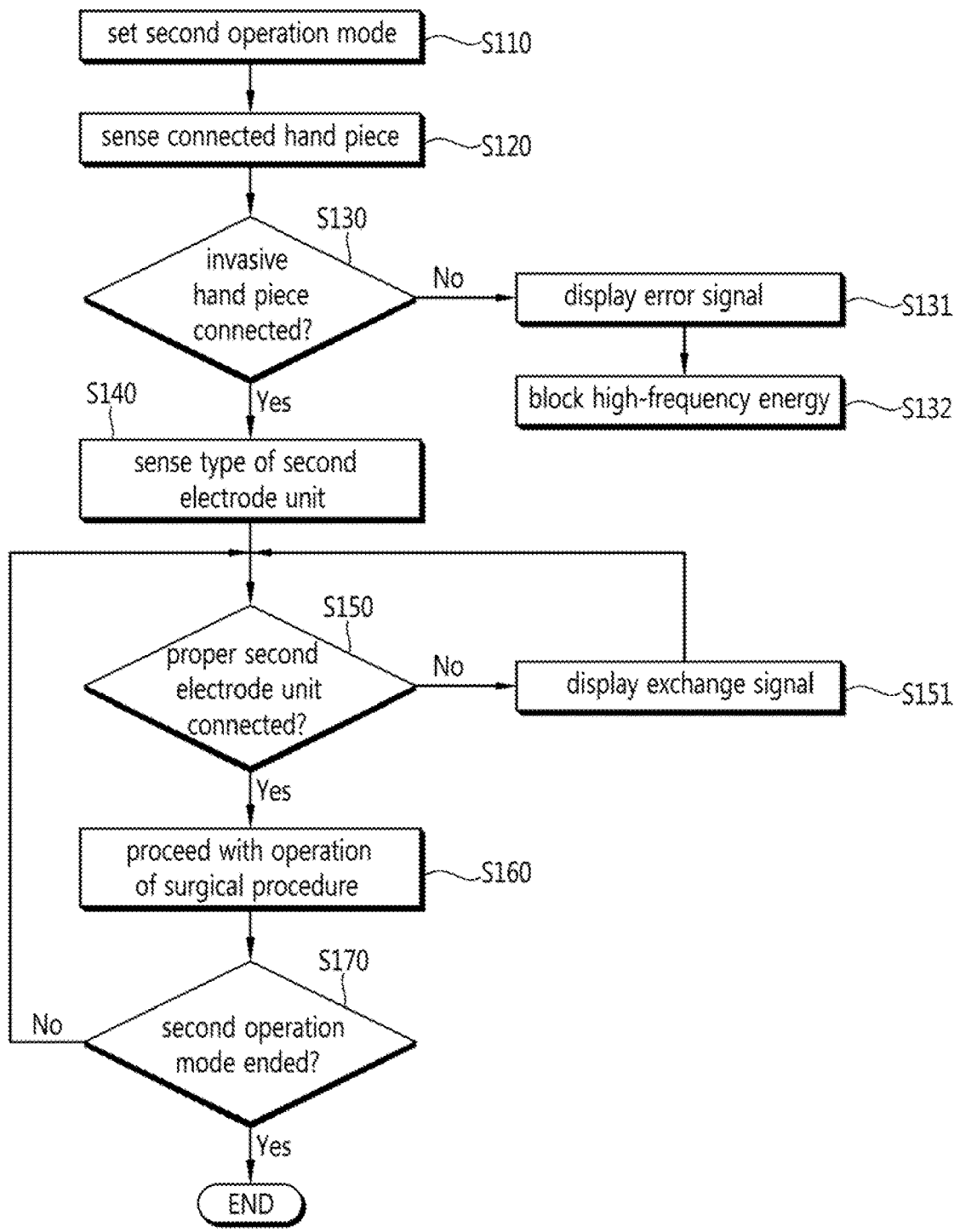
FIG. 9 is a flowchart illustrating a controlling method performed by a treatment device using high-frequency wave according to a second operation mode, in accordance with a first embodiment of the present invention.

Meanwhile, FIG. 9 illustrates a controlling method performed by a treatment device using high-frequency wave according to a second operation mode, in accordance with a first embodiment of the present invention. In such case, a user may set the treating device to operate in a second operation mode that uses the invasive hand piece 400 through the control panel 140 (S110).

If the operation mode is set, the sensing unit 130, as described above, senses the type of the hand piece coupled with the coupling unit 160 (S120) and transmits the sensed information to the controller 120 (S130). If determining that the contact-type hand piece 300 not corresponding to the second operation mode is coupled with the coupling unit 160, the controller 120 generates an error signal to inform the user (S131). Further, the controller 120 may limit high-frequency energy being provided to the contact-type hand piece 300 (S132).

Meanwhile, if determining that the sensed hand piece is the invasive hand piece 400, the controller 120 controls various elements so that the operation for a surgical procedure can proceed normally (S160).

However, as described above, the invasive hand piece 400 may be configured so that the second electrode unit 420 is exchangeably provided and thus one may be picked up for use among various second electrode unit modules configured to have a diversity of forms depending to the surgical procedure. An end of the invasive hand piece 400 has a second sensor 440 that may sense the type of the second electrode unit 420.

Accordingly, prior to going further to the surgical procedure, the invasive hand piece 400, specifically, the second sensor 440 may sense the type of the second electrode unit 420, and the controller 120 may determine whether the type of the second electrode unit sensed by the second sensor 440 corresponds to the second operation mode (S150).

The controller 120, if determining that the second electrode unit 420 currently provided does not correspond to the second operation mode, may generate an exchange signal and notify this to the user (S151). In contrast, when determining that the second electrode corresponds to the second operation mode, the controller 120 may perform control so that a normal operation for the surgical procedure is initiated.

Thereafter, the controller 120 determines whether the set second operation mode reaches its operation end time, and if so, may terminate the operation of various elements (S170).

A treatment device using high-frequency wave according to a second embodiment of the present invention is now described with reference to FIGS. 10 and 11. However, the components respectively corresponding to the components described above in connection with the first embodiment are referred to by the same denotations, and the description of similar configurations will be skipped to avoid duplication.

Figure 10:
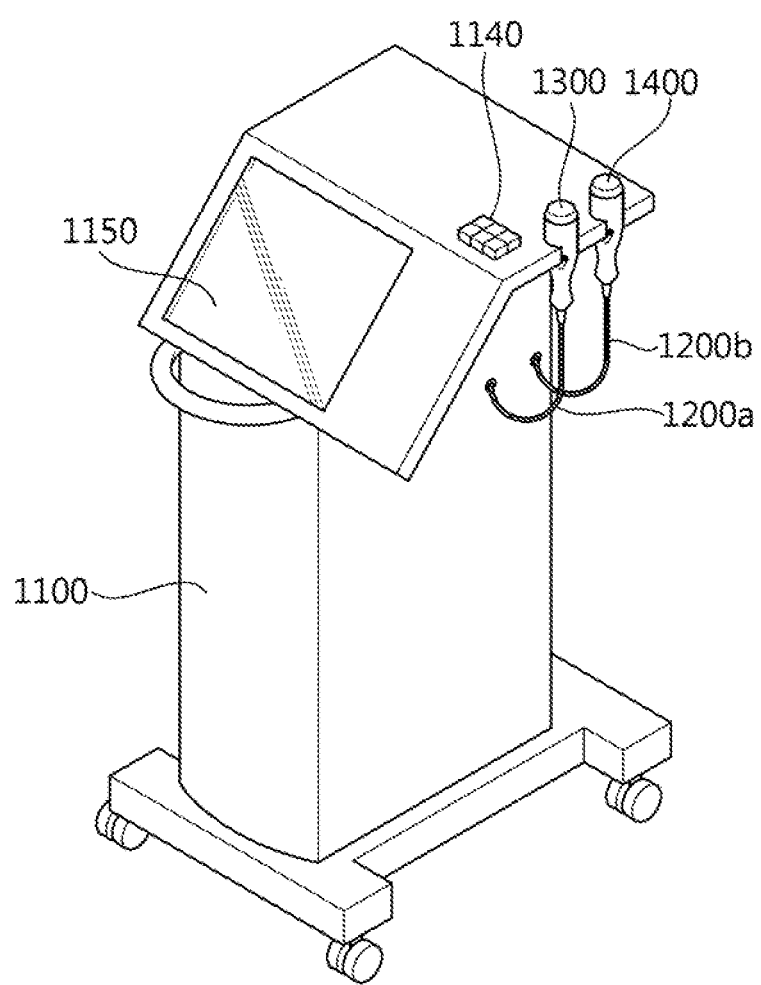
FIG. 10 is a perspective view illustrating a treatment device using high-frequency wave according to a second embodiment of the present invention.
Figure 11:
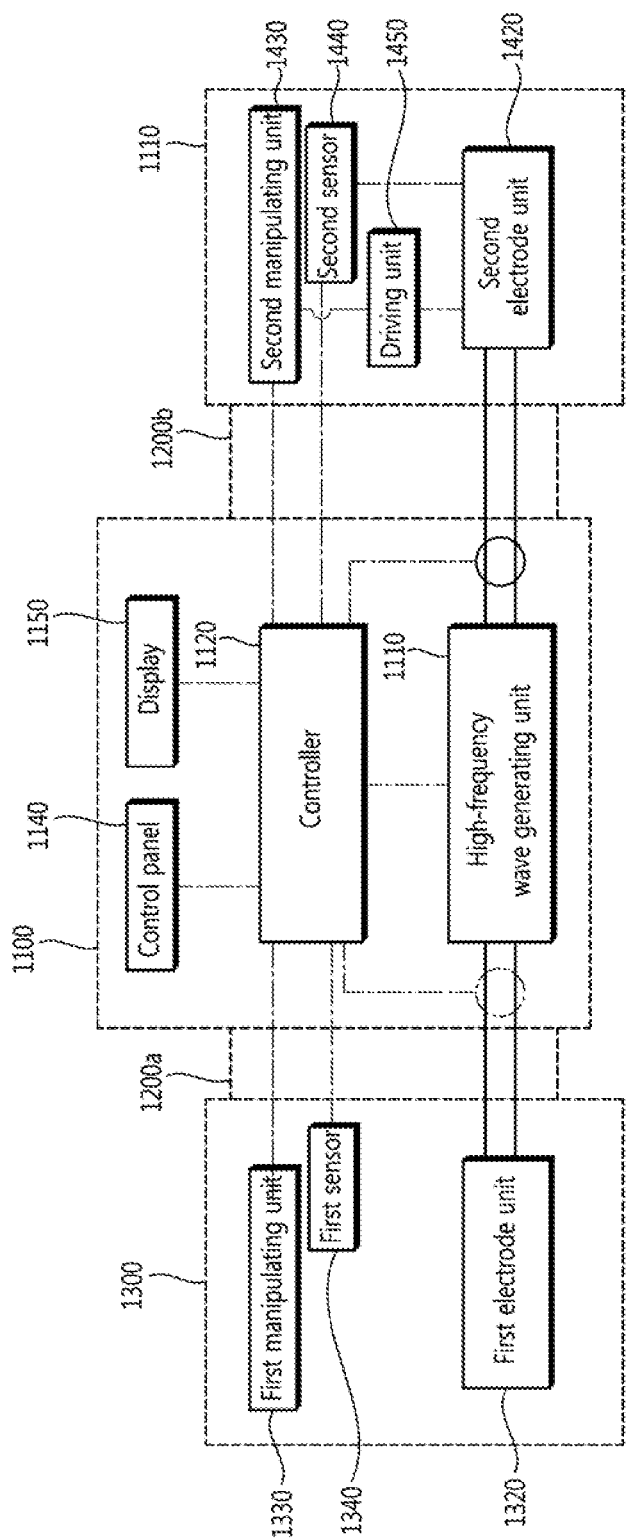
FIG. 11 is a view schematically illustrating the configuration of a treatment device using high-frequency wave as illustrated in FIG. 10.

FIG. 10 is a perspective view illustrating a treatment device using high-frequency wave according to a second embodiment of the present invention, and FIG. 11 is a view schematically illustrating the configuration of a treatment device using high-frequency wave as illustrated in FIG. 10.

In the above-described first embodiment, a contact-type hand piece and an invasive hand piece are selectively coupled with one treatment device using high-frequency wave. In the instant embodiment, however, each of a contact-type hand piece 1300 and an invasive hand piece 1400 is connected with one treatment device using high-frequency wave, as illustrated in FIG. 10.

As illustrated in FIG. 11, the main body 1100 includes a high-frequency wave generating unit 1110 that may provide high-frequency energy to a first electrode unit 1320 of the contact-type hand piece 1300 and a second electrode unit 1420 of the invasive hand piece 1400. The main body 1100 further includes a control panel 1140 that allows a user to set an operation mode and a display 1150 for displaying various pieces of information and the driving of the treating device. The controller 1120 is connected with various circuit elements such as a relay element 1170 that is provided over the path along which high-frequency energy is delivered, as well as the high-frequency wave generating unit 1110, the control panel 1140, and the display 1150, and controls various elements provided in the main body.

The contact-type hand piece 1300 is connected with the main body 1100 via a first cable 1200a. The first electrode unit 1320 of the contact-type hand piece 1300 is electrically connected with the high-frequency wave generating unit 1110 of the main body 1100 through a high-frequency wave delivering unit 1210a provided in the first cable 1200a. A manipulating unit 1330 and a first sensor 1340 may be connected with the controller 1120 via a signal line 1220a provided in the first cable 1200a.

The invasive hand piece 1400 is connected with the main body 1100 via a second cable 1200b. The second electrode unit 1420 of the invasive hand piece 1400 is connected with the high-frequency wave generating unit 1110 of the main body through a high-frequency wave delivering unit 1210b provided in the second cable 1200b. A second manipulating unit 1430, a driving unit 1450 and a second sensor 1440 may be connected with the controller 1120 via a signal line 1220b provided in the second cable 1200b.

The configuration and control method of the contact-type hand piece 1300 and the invasive hand piece 1400 according to this embodiment have been described above in detail, and detailed description thereof is skipped.

Meanwhile, in the treatment device using high-frequency wave according to this embodiment, an operator selects the contact-type hand piece 1300 or the invasive hand piece 1400 and proceeds with a surgical procedure. Accordingly, control may be performed by the controller 1120 so that high-frequency energy generated from the high-frequency wave generating unit 1110 is selectively provided to the contact-type hand piece 1300 or the invasive hand piece 1400.

Here, the treatment device using high-frequency wave according to this electrode module further includes a sensing unit (not shown) that senses the type of a hand piece used by a user. The sensing unit, although not shown in the drawings, may be configured to have various forms.

By way of example, the sensing unit may be configured as a sensor module that is formed on an outside surface of the main body of the contact-type hand piece 1300 and the invasive hand piece 1400. Accordingly, the type of a hand piece to be used by the user may be determined by sensing a change in pressure applied, temperature or an electrical change. As another example, the sensing unit may be configured as a sensor module that is provided in a mount where the contact-type hand piece 1300 and the invasive hand piece 1400 are mounted. Accordingly, a change in pressure, which occurs when the user selects one of the contact-type hand piece 1300 and the invasive hand piece 1400 and detaches the selected one from the mount, may be sensed to make such a determination. Besides the above-described two examples, the sensing unit may be configured in other various ways.

Accordingly, the controller 1120 may control various elements including the high-frequency wave generating unit 1110 in different modes, depending on the information on the hand piece currently in use, as sensed by the sensing unit.

For example, if it is sensed that the user is about to use the contact-type hand piece 1300, the path along which high-frequency energy is supplied from the high-frequency wave generating unit 1110 to the invasive hand piece 1400 is blocked. Then, the signal line 1220a connected with the contact-type hand piece 1300 is activated, and the signal line 1220b connected with the invasive hand piece 1400 is deactivated.

As another example, if it is sensed that the user is about to use the invasive hand piece 1400, control may be performed to stop the operation of a high-frequency wave generating module (not shown) that is not used to provide high-frequency energy to the invasive hand piece 1400. The path along which high-frequency energy is provided from the high-frequency wave generating unit 1110 to the contact-type hand piece 1300 is then cut off. Further, the signal line 1220b connected with the invasive hand piece 1400 is activated, while the signal line 1220a connected with the contact-type hand piece 1300 is deactivated.

Further, the controller 1120, if an operation mode is set from the control panel 1140, compares the operation mode with hand piece information sensed by the sensing unit. Accordingly, if determining that the user is about to use a hand piece that does not correspond to the set operation mode, the controller 1120 may inform the user that an error has occurred through the display 1150 or a separate alert sound. The controller 1120 may then limit the operation of the high-frequency wave generating unit 1110 or block the path along which high-frequency energy is delivered from the high-frequency wave generating unit 1110. Meanwhile, if determining that the user uses a hand piece corresponding to the set operation mode, the controller 1120 may control the high-frequency wave generating unit 1110 and other various elements to be left in operation.

As such, even when two different hand pieces from each other are connected with one treatment device using high-frequency wave according to the embodiment, the controller 1120 may sense various elements based on the hand piece use information sensed by the sensing unit, thus leading to an optimized surgical procedure. Further, any security issue that may arise when a hand piece not corresponding to a set operation mode is used may be addressed.

Although some embodiments of the present invention have been described, it should be apparent to one of ordinary skill in the art that many changes in form and detail may be made thereto without departing from the scope or spirit of the invention defined by the following claims.

The invention claimed is:

1. A treatment device using high-frequency wave, comprising:
   a main body including a high-frequency wave generating unit;
   a contact-type hand piece detachably provided at a coupling unit of the main body, the contact-type hand piece having a first electrode unit that provides high-frequency energy generated from the high-frequency wave generating unit to a skin surface;
   an invasive hand piece detachably provided at the coupling unit of the main body, the invasive hand piece having a second electrode unit that provides high-frequency energy generated from the high-frequency wave generating unit to an inner portion under the skin;
   a controller controlling high-frequency energy provided from the high-frequency wave generating unit to the first electrode unit or the second electrode unit; and
   a sensing unit sensing a type of a hand piece connected with the coupling unit, of the contact-type hand piece and the invasive hand piece,
   wherein the invasive hand piece further includes a tilting unit that leads an end of the second electrode unit to penetrate into the skin surface with an inclination.

2. The treatment device using high-frequency wave of claim 1, wherein the controller compares a set operation mode with the type of the hand piece sensed by the sensing unit, and if determining that a hand piece corresponding to the set operation mode is not connected with the coupling unit, generates an error signal.

3. The treatment device using high-frequency wave of claim 2, wherein if determining that the hand piece corresponding to the set operation mode is not connected with the coupling unit, the controller controls not to provide the high-frequency energy from the high-frequency wave generating unit to the hand piece.

4. The treatment device using high-frequency wave of claim 1, wherein the controller controls the high-frequency wave generating unit in different modes from each other depending on the type of the hand piece sensed by the sensing unit.

5. The treatment device using high-frequency wave of claim 1, wherein the contact-type hand piece includes a first sensor that senses a contact state between the first electrode unit and the skin, and wherein if determining that the contact state between the first electrode unit and the skin is poor, based on information sensed by the first sensor, the controller generates a contact-poor signal.

6. The treatment device using high-frequency wave of claim 1, wherein the first electrode unit of the contact-type hand piece includes a plurality of electrode modules, wherein the high-frequency wave generating unit includes a plurality of high-frequency wave generating modules respectively corresponding to the plurality of electrode modules, and wherein the controller independently controls the plurality of electrode modules so that different frequencies of high-frequency energy are provided to the skin surface through the plurality of electrode modules.

7. The treatment device using high-frequency wave of claim 1, wherein the second electrode unit is exchangeably provided at the invasive hand piece, and wherein the invasive hand piece further includes a second sensor that senses a type of the second electrode unit.

8. The treatment device using high-frequency wave of claim 7, wherein the controller compares a set operation mode with the type of the second electrode unit sensed by the second sensor, and if determining that the second electrode unit provided at the invasive hand piece does not correspond to the set operation mode, generates an error signal.

9. The treatment device using high-frequency wave of claim 7, wherein the controller controls the high-frequency wave generating unit in different modes from each other depending on the type of the second electrode unit sensed by the second sensor.

10. The treatment device using high-frequency wave of claim 1, wherein the tilting unit includes at least one or more elastomers that are arranged at a rear surface of the second electrode unit, and wherein an elastic modulus at, at least, one position on the rear surface of the second electrode unit is different from an elastic modulus at an adjacent position.

11. The treatment device using high-frequency wave of claim 1, wherein the tilting unit includes at least one or more elastomers that are arranged at a rear surface of the second electrode unit.

* * * * *